United States Patent

Warren et al.

[11] 3,953,604
[45] Apr. 27, 1976

[54] 1-(2-SUBSTITUTED-CHROMONYLOXY)-2-HYDROXY-3-(SUBSTITUTED PHENOXY)PROPANES

[75] Inventors: Brian Thomas Warren, Ickenham; John William Spicer, London, both of England

[73] Assignee: Miles Laboratories, Inc., Elkhart, Ind.

[22] Filed: Dec. 3, 1973

[21] Appl. No.: 421,497

Related U.S. Application Data

[62] Division of Ser. No. 320,600, Jan. 2, 1973, Pat. No. 3,899,513.

[52] U.S. Cl. .............................. 424/283
[51] Int. Cl.² ........................... A61K 31/35
[58] Field of Search ................... 424/283

[56] References Cited
UNITED STATES PATENTS

| | | | |
|---|---|---|---|
| 3,519,652 | 7/1970 | Fitzmaurice et al. | 260/345.2 |
| 3,673,218 | 6/1972 | Cairns et al. | 260/345.2 |
| 3,792,063 | 2/1974 | Cairns et al. | 260/345.2 |
| 3,823,165 | 7/1974 | Cairns et al. | 260/345.2 |

OTHER PUBLICATIONS
Physicians Desk Reference (PDR) 1974, p. 760.

*Primary Examiner*—Norman A. Drezin
*Attorney, Agent, or Firm*—Myron B. Sokolowski

[57] ABSTRACT

Definitions: in the following Formulae I, II and IV, $R^1$ represents hydrogen, alkyl of 1 to 4 carbon atoms, or a nontoxic cation, while each of $R^2$, $R^3$, $R^4$, $R^5$, and $R^6$ symbolizes hydrogen, alkyl of 1 to 4 carbon atoms, alkoxy of 1 to 4 carbon atoms, carboxy, carbalkoxy of 1 to 4 carbon atoms, trihalomethyl, halogen, nitro or cyano.

Certain 1-(2-substituted-chromon-yloxy)-2-hydroxy-3-(substituted-phenoxy)propanes (Formula I),

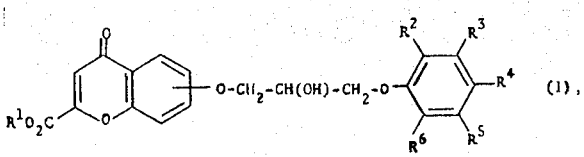

can be synthesized from intermediate bis-(substituted-phenoxy)propanes (Formula II),

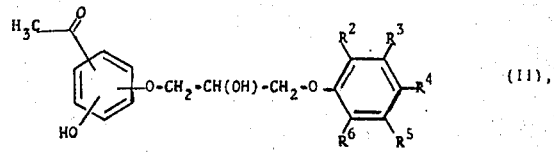

by condensation with diethyl oxalate in the presence of sodium ethoxide followed by cyclization with a mixture of glacial acetic acid and concentrated sulfuric or a mixture of concentrated hydrochloric acid and a lower alcohol containing up to 4 carbon atoms.

The bis-(substituted-phenoxy)propane intermediates (Formula II) are prepared by reacting a dihydroxyacetophenone (Formula III),

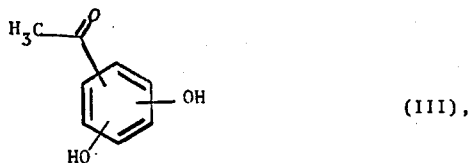

with a (substituted-phenyl)glycidyl ether (Formula IV),

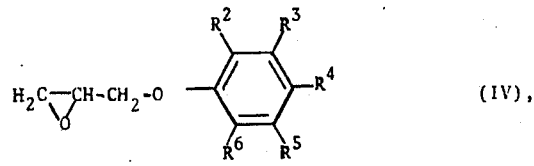

in an organic solvent in the presence of a catalyst.

The 1-(2-substituted-chromon-yloxy)-2-hydroxy-3-(substituted-phenoxy)propanes (Formula I) are useful in the treatment of allergic conditions in mammals. The bis-(substituted-phenoxy)propanes (Formula II) are useful as intermediates in the synthesis of the latter compounds. Methods of preparing compounds having Formulae I and II are described. Methods of treating allergic conditions in mammals utilizing compounds of Formula I are also disclosed.

2 Claims, No Drawings

1-(2-SUBSTITUTED-CHROMONYLOXY)-2-HYDROXY-3-(SUBSTITUTED PHENOXY)PROPANES

This is a division of application Ser. No. 320,600, filed Jan. 2, 1973, now U.S. Pat. No. 3,899,513.

BACKGROUND OF THE INVENTION

1. Field of the Invention

Allergic asthma, hay fever, and other anaphylactic conditions are treated by a variety of chemotherapeutic agents, of which the following are representative: certain xanthine compounds, particularly aminophylline; some sympathomimetic amines, such as epinephrine; selected cortico-steroids; and disodium cromoglycate.

The disclosed 1-(2-substituted-chromon-yloxy)-2-hydroxy-3-(substituted-phenoxy)propanes demonstrate therapeutic utility in the treatment of such allergic conditions.

2. Description of the Prior Art

Khellin, 4,9-dimethoxy-7-methyl-5H-furo[3,2-g] [1] benzo-pyran-5 one (Formula V),

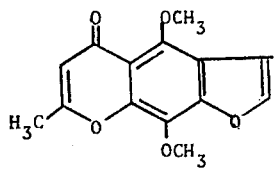

was first isolated, and its structure determined, by Späth and Gruber (Ber. 71: 106 [1938]). Khellin subsequently was utilized as a coronary vasodilator, as a bronchodilator, and as an agent for the treatment of colic.

Structural modifications of Khellin led to the synthesis of 5-alkoxy substituted chromone-2-carboxylic acids (Formula VI),

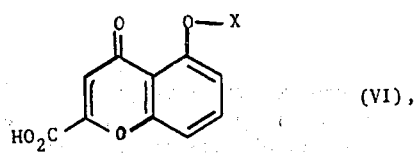

wherein X can be a variety of substituted alkyl sidechains. Compounds of Formula VI are disclosed by Ellis and Wragg and by Fitzmaurice et al. in British Patent No. 1,049,289 (1966) and No. 1,093,673 (1967) respectively. Such chromone derivatives exhibit biological activity in the treatment of allergic conditions, but such activity is of short duration (see Cox et al., Adv. Drug Res., 5: 118 [1970]). Because of the latter property, the 5-alkoxy substituted chromone-2-carboxylic acids had limited usefulness.

Clinically useful substituted bis-(2-carboxy-chromon-yloxy) derivatives were described by Fitzmaurice et al. in British Patent No. 1,144,905 (1969), particularly disodium chromoglycate, or 1,3-di(2-carboxy-4-oxochromon-5-yloxy)-2-hydroxy-propane disodium salt (Formula VII)

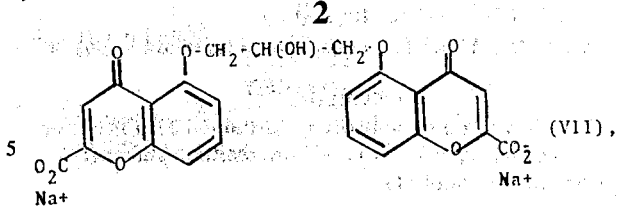

Disodium chromoglycate, known commercially as Intal, is used to treat allergic bronchial asthma. It produces, however, several untoward side effects.

SUMMARY OF THE INVENTION

Definitions

The following definitions apply throughout this Summary:

a. In any structural formula presented in the Summary, $R^1$ represents hydrogen, alkyl of 1 to 4 carbon atoms, or nontoxic pharmaceutically acceptable cations.

b. Also in any structural formula, $R^2$, $R^3$, $R^4$, $R^5$, and $R^6$ each represent hydrogen, alkyl of 1 to 4 carbon atoms, carboxy, carbalkoxy of 1 to 4 carbon atoms, trihalomethyl, halogen, nitro, cyano or alkoxy of 1 to 4 carbon atoms.

c. Carbon atom positions in ring moieties of the compounds disclosed are numbered clockwise; where the ring moiety is heteropolycyclic, the hetero-atom is assigned the number one (1), and all other atoms in the ring are numbered sequentially in a clockwise manner, excluding atoms at ring junctures; to illustrate, chromone (benzo-γ-pyrone) is numbered as follows:

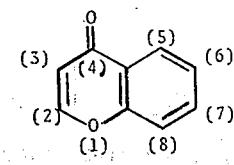

d. The term "2-substituted-chromon-yloxy moiety" refers to the following chemical formula

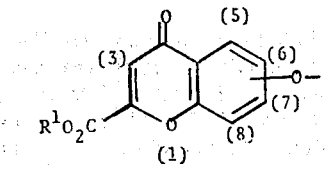

Designation of the carbon atoms in this structure follows the definition (c), supra. $R^1$ is defined in (a), supra.

e. The term "substituted-phenoxy moiety" refers to the structure

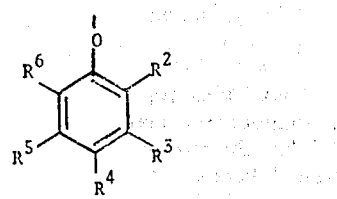

wherein $R^2$, $R^3$, $R^4$, $R^5$, and $R^6$ are defined in (b), supra.

SUMMARY

This invention comprises certain 1-(2-substituted-chromon-yloxy)-2-hydroxy-3-(substituted-phenoxy)-propanes (Formula I):

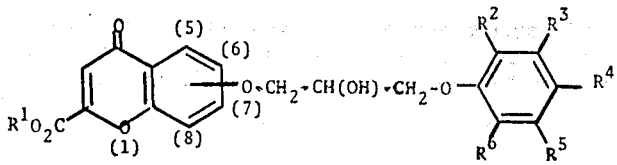

(I).

The 2-substituted-chromon-yloxy moiety is bonded to the remainder of Formula I at carbon atom positions 5, 6, 7, or 8. Bonding at positions 5, 6, or 7 is preferred, as represented by Formulae (Ia), (Ib), and (Ic):

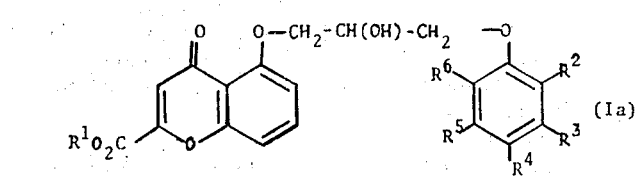

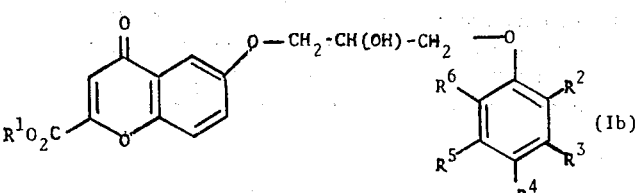

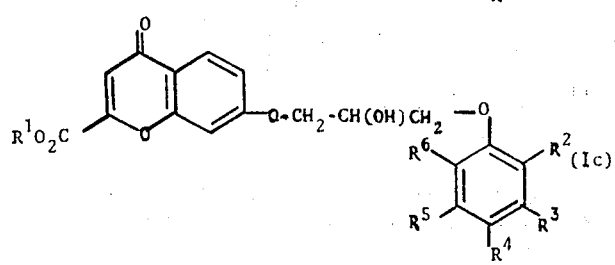

In the substituted-phenoxy moiety of Formula I, each of $R^2$, $R^3$, $R^4$, $R^5$ and $R^6$ is a substituent as defined in the Definitions above. It is preferred that: (a) either all substituents $R^2$ through $R^6$, inclusive, are hydrogen; or (b) only 3 of substituents $R^2$ through $R^6$ inclusive, are hydrogen while the other two substituents are other than hydrogen. Among the preferred embodiments of the substituted-phenoxy moiety of Formula I are the following:

phenoxy
p-bromophenoxy
p-chlorophenoxy
p-fluorophenoxy
p-methoxyphenoxy
m-cresyloxy
o-cresyloxy
p-(t-butyl)phenoxy
2,6-dimethylphenoxy
2,5-dimethylphenoxy
p-ethylphenoxy
o-(n-propyl)phenoxy
m-trifluoromethylphenoxy
p-carbethoxyphenoxy
p-cyanophenoxy
p-nitrophenoxy
2,4-dichlorophenoxy
3-methoxy-4-cyanophenoxy
3-methoxy-4-carboxyphenoxy
3-methoxy-4-carbethoxyphenoxy Preferred embodiments of Formula I include the following compounds:

1-(2-carboxychromon-5-yloxy)-2-hydroxy-3-phenoxypropane, the ethyl ester and the sodium salt thereof (Examples 2, 3, 4);

1-(2-carboxychromon-5-yloxy)-2-hydroxy-3-p-bromophenoxy-propane, the ethyl ester, and the sodium salt thereof (Examples 6, 7, 8);

1-(2-carboxychromon-5-yloxy)-2-hydroxy-3-p-chlorophenoxy-propane, and the ethyl ester thereof (Examples 10 and 11);

1-(2-carboxychromon-5-yloxy)-2-hydroxy-3-p-methoxy-phenoxypropane, the ethyl ester, and the sodium salt thereof (Examples 13, 14, 15);

1-(2-carboxychromon-5-yloxy)-2-hydroxy-3-o-cresyloxy-propane, the ethyl ester and the sodium salt thereof (Examples 17, 18, 19);

1-(2-carboxychromon-5-yloxy)-2-hydroxy-3-p-(t-butyl) phenoxypropane, the ethyl ester, and the sodium salt thereof (Examples 21, 22, 23);

1-(2-carboxychromon-5-yloxy)-2-hydroxy-3-(2,6-dimethyl(-phenoxy)propane and the ethyl ester thereof (Examples 25 and 26);
1-(2-carboxychromon-5-yloxy)-2-hydroxy-3-m-cresyloxy-propane and the ethyl ester thereof (Examples 28 and 29);
1-(2-carboxychromon-5-yloxy)-2-hydroxy-3-p-ethylphenoxy-propane sodium salt and ethyl ester (Examples 31 and 32);
1-(2-carboxychromon-5-yloxy)-2-hydroxy-3-p-cyanophenoxy-propane sodium salt and ethyl ester (Examples 34 and 35);
1-(2-carboxychromon-5-yloxy)-2-hydroxy-3-p-nitrophenoxy-propane sodium salt and ethyl ester (Examples 37 and 38); 1-(2-carboxychromon-7-yloxy)-2-hydroxy-3-phenoxypropane and the sodium salt thereof (Examples 40 and 41);
1-(2-carboxychromon-5-yloxy)-2-hydroxy-3-p-ethoxyphenoxy-propane and the sodium salt thereof (Examples 42 and 44);
1-(2-carboxychromon-5-yloxy)-2-hydroxy-3-(2,5-dimethyl-phenoxy)propane sodium salt and ethyl ester (Examples 46 and 47);
1-(2-carboxychromon-5-yloxy)-2-hydroxy-3-o-(n-propyl) phenoxypropane sodium salt and ethyl ester (Examples 49 and 50);
1-(2-carboxychromon-7-yloxy)-2-hydroxy-3-p-cyanophenoxy-propane sodium salt and ethyl ester (Examples 52 and 53);
1-(2-carboxychromon-6-yloxy)-2-hydroxy-3-p-cyanophenoxy-propane sodium salt and ethyl ester (Examples 55 and 56);
1-(2-carboxychromon-5-yloxy)-2-hydroxy-3-m-trifluoro-methylphenoxypropane sodium salt and ethyl ester (Examples 58 and 59);
1-(2-carboxychromon-5-yloxy)-2-hydroxy-3-(2,4-dichloro-phenoxy)propane sodium salt and ethyl ester (Examples 61 and 62);
1-(2-carboxychromon-5-yloxy)-2-hydroxy-p-fluorophenoxy-propane sodium salt and ethyl ester (Examples 64 and 65);
1-(2-carboxychromon-5-yloxy)-2-hydroxy-3-(3-methoxy-4-cyanophenoxy)propane sodium salt and ethyl ester (Examples 67 and 68);
1-(2-carboxychromon-5-yloxy)-2-hydroxy-3-(3-methoxy-4-carbethoxyphenoxy)propane sodium salt and ethyl ester; and
1-(2-carboxychromon-5-yloxy)-2-hydroxy-3-(3-methoxy-4-carboxyphenoxy)propane disodium salt and ethyl ester.

Compounds having Formula (I) display anti-allergic properties in mammals, and are useful in the treatment of allergic asthma, hayfever, and other allergic or anaphylactic conditions. Details of such activity are delineated in Examples 69, 70, and 71 in the Description of the Preferred Embodiments, infra.

Dose forms of compounds of Formula (I) can be prepared in compositions by the addition of pharmaceutically acceptable carriers generally used in the formation of pharmaceutical compositions. Such compositions can be prepared in the solid or liquid state by methods known in the art for administration by inhalation, ingestion, intravenous or parenteral injection, and by other means. For the treatment of asthma, the compositions may be in a form suitable for administration by inhalation. Thus the compositions may comprise a suspension or solution of the 1-(2-substituted -chromon-yloxy)-2-hydroxy-3-(substituted-phenoxy)propane in water or in a suitable alcohol for administration as an aerosol by means of a conventional nebuliser. Alternatively, the compositions may comprise a suspension or solution of the active ingredient in a conventional liquefied propellant to be administered as an aerosol from a pressurized container. The compositions may also comprise the solid active ingredient in a solid diluent for administration from a powder inhalation device. Other routes of administration, e.g. sublingual, oral or buccal tablets, rectal suppositories or intravenous injection or infusion may also be used.

The compositions may also contain, in addition to the compound of general Formula I, other active ingredients, for instance other bronchodilators. These additional bronchodialtors can include those of the $\beta$-adrenergic type, such as iso- or orci-prenaline, salbutamol, or a pharmaceutically acceptable salt thereof. The compositions may contain 0.1 to 10% by weight of the compound of Formula I. If salbutamol or iso- or orci-prenaline sulphate is used, it is suitably present in a concentration of 0.1 to 5% by weight.

Compounds of Formula I can be prepared from bis-(substituted-phenoxy)propanes (Formula II),

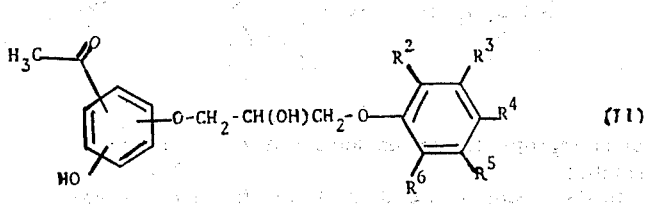

by condensation with diethyl oxalate in the presence of sodium ethoxide, followed by cyclization with a mixture of glacial acetic and concentrated sulfuric acids to obtain the acid form of Formula I (i.e. $R^1$ is hydrogen), or a mixture of concentrated hydrochloric acid and a lower alcohol of 1 to 4 carbon atoms to obtain the ester form of Formula I (i.e. $R^1$ is lower alkyl of 1 to 4 carbon atoms). Nontoxic, pharmaceutically acceptable salts of Formula I (i.e. $R^1$ is a nontoxic cation) can be prepared from the acid form by reacting the latter with a carbonate solution having the desired cationic species or from the ester forms by saponification. In the above process, Formula II has the following preferred embodiments:

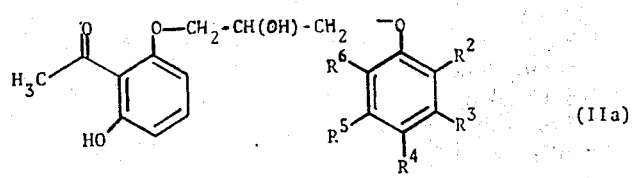

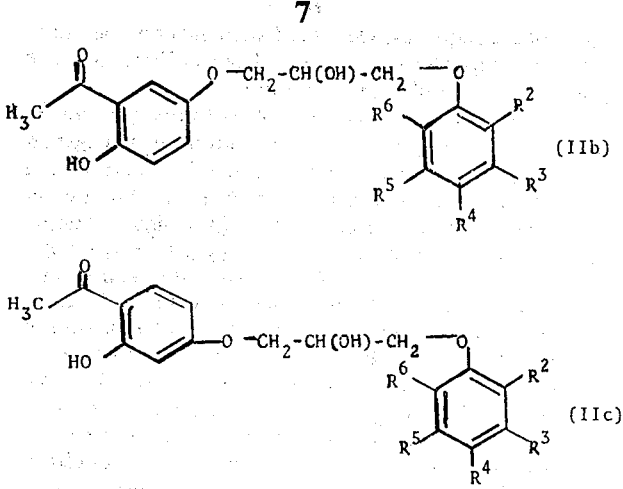

(IIb)

(IIc)

Compounds having Formula II are useful in the preparation of compounds represented by Formula I, and can be synthesized by reacting a dihydroxyacetophenone (Formula III),

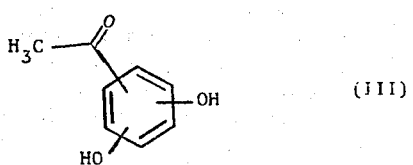

(III)

with a (substituted-phenyl)glycidyl ether (Formula IV),

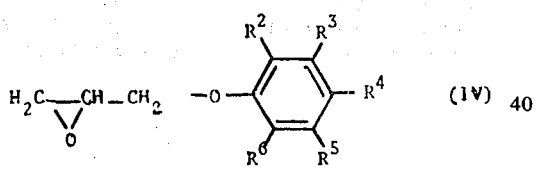

(IV)

in an appropriate organic solvent in the presence of a catalyst.

In the synthesis described above, the following are preferred embodiments:

a. The dihydroxyacetophenone (Formula III) is 2,6-dihydroxyacetophenone, 2,4-dihydroxyacetophenone, or 2,5-dihydroxyacetophenone.
b. The organic solvent is 2-ethoxyethanol.
c. The catalyst is benzyltrimethylammonium hydroxide.
d. The reaction is performed under reflux.
e. The following are preferred substituted-phenyl moieties in Formula IV
    phenyl
    p-bromophenyl
    p-chlorophenyl
    p-fluorophenyl
    p-methylphenyl
    m-cresyl
    o-cresyl
    p-(t-butyl)phenyl
    2,6-dimethylphenyl
    2,5-dimethylphenyl
    p-ethylphenyl
    o-(n-propyl)phenyl
    m-trifluoromethylphenyl
    p-carbethoxyphenyl
    p-carboxyphenyl
    p-cyanophenyl
    2,4-dichlorophenyl
    3-methoxy-4-carbethoxyphenyl
    3-methoxy-4-cyanophenyl
    3-methoxy-4-carboxyphenyl Preferred embodiments of Formula IIa include:
1-(2-acetyl-3-hydroxyphenoxy)-2-hydroxy-3-phenoxypropane (Example 1; Intermediate to Examples 2, 3, and 4);
1-(2-acetyl-3-hydroxyphenoxy)-2-hydroxy-p-bromophenoxypropane (Example 5; Intermediate to Examples 6, 7 and 8);
1-(2-acetyl-3-hydroxyphenoxy)-2-hydroxy-p-chlorophenoxypropane (Example 9; Intermediate to Examples 10 and 11);
1-(2-acetyl-3-hydroxyphenoxy)-2-hydroxy-p-methoxyphenoxypropane (Example 12; Intermediate to Examples 13, 14, and 15);
1-(2-acetyl-3-hydroxyphenoxy)-2-hydroxy-o-cresyloxypropane (Examples 16; Intermediate to Examples 17, 18, and 19);
1-(2-acetyl-3-hydroxyphenoxy)-2-hydroxy-t-butylphenoxypropane (Example 20; Intermediate to Examples 21, 22, and 23);
1-(2-acetyl-3-hydroxyphenoxy)-2-hydroxy-2,6-dimethylphenoxypropane (Examples 24; Intermediate to Examples 25 and 26);
1-(2-acetyl-3-hydroxyphenoxy)-2-hydroxy-m-cresyloxypropane (Example 27; Intermediate to Examples 28 and 29);
1-(2-acetyl-3-hydroxyphenoxy-2-hydroxy-p-ethylphenoxypropane (Example 30; Intermediate to Examples 31 and 32);
1-(2-acetyl-3-hydroxyphenoxy)-2-hydroxy-3-p-cyanophenoxypropane (Example 33; Intermediate to Examples 34 and 35);
1-(2-acetyl-3-hydroxyphenoxy)-2-hydroxy-3-p-carbethoxyphenoxypropane (Example 42; Intermediaate to Examples 43 and 44);
1-(2-acetyl-3-hydroxyphenoxy)-2-hydroxy-3-(2,5-dimethylphenoxy)propane (Example 45; Intermediate to Examples 46 and 47);
1-(2-acetyl-3-hydroxyphenoxy)-2-hydroxy-3-(2-n-propylphenoxy)propane (Example 48; Intermediate to Examples 49 and 50);
1(2-acetyl-3-hydroxyphenoxy)-2-hydroxy-3-(m-trifluoromethylphenoxy)propane (Example 57; Intermediate to Examples 58 to 59);
1-(2-acetyl-3-hydroxyphenoxy)-2-hydroxy-3-(2,4-dichlorophenoxy)propane (Example 60; Intermediate to Examples 61 and 62);
1-(2-acetyl-3-hydroxyphenoxy)-2-hydroxy-3-p-fluorophenoxypropane (Example 63; Intermediate to Examples 64 and 65);
1-(2-acetyl-3-hydroxyphenoxy)-2-hydroxy-3-(3-methoxy-4-cyanophenoxy)propane (Example 66; Intermediate to Examples 67 and 68);
1-(2-acetyl-3-hydroxyphenoxy)-2-hydroxy-3-(3-methoxy-4-carboxyphenoxy)propane; and
1(2-acetyl-3-hydroxyphenoxy)-2-hydroxy-3-(3-methoxy-4-carbethoxyphenoxy)propane.

Preferred embodiments of Formula IIb include:
1(3-acetyl-4-hydroxyphenoxy)-2-hydroxy-3-phenoxypropane (Example 39; Intermediate to Examples 40 and 41); and
1-(3-acetyl-4-hydroxyphenoxy)-2-hydroxy-3-p-cyanophenoxypropane (Example 51; Intermediate to Examples 52 and 53).

Preferred embodiments of Formula IIc include:
1-(3-hydroxy-4-acetylphenoxy)-2-hydroxy-3-phenoxypropane (Example 54; Intermediate to Examples 55 and 56).

DESCRIPTION OF THE PREFERRED EMBODIMENTS

EXAMPLE 1

1-(2-Acetyl-3-hydroxyphenoxy)-2-Hydroxy-3-Phenoxypropane

A solution of 2,6-dihydroxyacetophenone (15.2g.), phenylglycidyl ether (15.0 g) and benzyltrimethylammonium hydroxide (5 drops of a 40% solution) in 2-ethoxyethanol (75 ml) was heated under reflux for 48 hours. The solvent was removed under reduced pressure and the resulting solid was washed with ether. Recrystallization from aqueous ethanol gave 1-(2-acetyl-3-hydroxyphenoxy(-2-hydroxy-3-phenoxypropane, 19.0 g, as pale lemon needles, m.p. 100.5°–101.5° C.

Analysis: Found: C, 67.4%; H, 6.0%. $C_{17}H_{18}O_5$ requires: C 67.6% H, 6.0%.

EXAMPLE 2

1-(2-Carboxychromon-5-yloxy)-2-Hydroxy-3-Phenoxypropane.

A solution of 1-(2-acetyl-3-hydroxyphenoxy)-2-hydroxy-3-phenoxypropane (12.08 g) in diethyl oxalate (30 ml) was added to a suspension of sodium ethoxide, prepared from sodium (6.0 g) and ethanol (60 ml), in benzene (100 ml). The mixture was heated under reflux for 1.5 hours, cooled and poured into ether. The precipitated yellow solid was collected, washed with ether and dried. The solid was then added to a mixture of glacial acetic acid (80 ml) and concentrated hydrochloric acid (30 ml) and heated under reflux for 1 hour. After cooling, the reaction mixture was poured with stirring into cold water (1 L). The precipitated gum was washed with water by decantation and solidified by trituration with acetic acid. Recrystallization from acetic acid gave 1-(2-carboxychromon-5-yloxy)-2-hydroxy-3-phenoxypropane (7.0 g) as a white powder, m.p. 88°–90° C.

Analysis: Found: C, 59.4%; H, 4.9%. $C_{19}H_{16}O_7 \cdot 3/2H_2O$ requires: $C_{59.5}\%$; $H_{4.9}\%$.

EXAMPLE 3

1-(2-Carbethoxychromon-5-yloxy)-2-Hydroxy-3-Phenoxypropane

A mixture of 1-(2-carboxychromon-5-yloxy)-2-hydroxy-3-phenoxypropane (10.0 g), ethanol (5 ml), benzene (100 ml) and concentrated sulphuric acid (5 drops) was heated under reflux for 6 hours, the water that formed being collected in a phase separator. The cooled solution was washed with saturated sodium bicarbonate solution and water. Removal of the benzene under reduced pressure yielded 1-(2-carbethoxychromon-5-yloxy)-2-hydroxy-2-phenoxypropane as a viscous oil.

EXAMPLE 4

1-(2-Carboxychromon-5-yloxy)-2-Hydroxy-3-Phenoxypropane Sodium Salt

A solution of sodium hydroxide (0.6 g) in ethanol (100 ml) was added to 1-(2-carbethoxychromon-5-yloxy)-2-hydroxy-3-phenoxypropane (5.7 g) and the mixture was heated under reflux on a water bath for 1 hour. The solid that separated was filtered off and recrystallized from water (charcoal) to give 1-(2-carboxychromon-5-yloxy)-2-hydroxy-3-phenoxypropane sodium salt, (2.3 g), a slightly pink solid, m.p. 221°–223° C.

Analysis: Found: C, 60.42%, H, 4.61%. $C_{19}H_{15}O_7Na$ requires: C, 60.3%; $H_{3.98}\%$.

EXAMPLE 5

1-(2-Acetyl-3-hydroxyphenoxy)-2-Hydorxy-3-p-Bromophenoxypropane

A solution of 2,6-dihydroxyacetophenone (15.2 g) and p-bromophenylglycidyl ether (22.9 g) in 2-ethoxyethanol (75 ml) containing benzyltrimethylammonium hydroxide solution (10 drops: 40%) was heated under reflux for 72 hours. The solvent was removed by distillation under reduced pressure and the residual viscous orange oil was allowed to stand overnight during which time crystallization commenced. The residue was triturated with diethyl ether and the solid collected. 1-(2-acetyl-3-hydroxy-phenoxy)-2-hydroxy-2-p-bromophenoxypropane, was obtained as a pale yellow solid, 16.4 g; m.p. 101.5°–103° C.

Analysis: Found: C, 53.8%; H, 4.5%, Br, 21.1% $C_{17}H_{17}BrO$ requires: C, 53.6%; H, 4.5%; Br, 21.6%

EXAMPLE 6

1-(2-Carbethoxychromon-5-yloxy)-2-Hydroxy-3-p-Bromophenoxypropane

A mixture of 1-(2-acetyl-3-hydroxyphenoxy)-2-hydroxy-3-p-bromophenoxypropane (15.2 g) and diethyl oxalate (15 ml) was added to a suspension of sodium ethoxide (prepared from 3.0 sodium) in absolute ether. The mixture was heated under reflux for 1.5 hours and then poured onto ice (100 g). After acidification with a solution of acetic acid (12 ml) in water (80 ml), the ether layer was separated and the aqueous layer was extracted with ether (3 × 25 ml). The combined ether solutions were evaporated and the residue was dissolved in a mixture of acetic acid (80 ml) and hydrochloric acid (30 ml) and heated under reflux for 1 hour. Recrystallization from acetic acid yielded crude 1-(2-carboxychromon-5-yloxy)-2-hydroxy-3-p-bromophenoxypropane, (14.7 g), as a white solid, m.p.

188°–190°, which was converted to the ethyl ester employing absolute ethyl alcohol and concentrated sulphuric acid as catalyst. 1-(2-carbethoxychromon-5-yloxy)-2-hydroxy-2-p-bromophenoxypropane was obtained as white crystals, m.p. 79°–80° after recrystallization from aqueous dioxane.

Analysis: Found: C, 54.05%; H, 4.32%; Br, 17.06%. $C_{21}H_{19}BrO_7$ requires: C, 54.4%; H, 4.1%; Br, 17.25%.

EXAMPLE 7

1-(2-Carboxychromon-5-yloxy-2-Hydroxy-3-p-Bromophenoxypropane

A solution of sodium hydroxide (0.6 g) in ethanol (100 ml) was added to 1-(2-carbethoxychromon-5-yloxy)-2-hydroxy-3-p-bromophenoxypropane (6.6 g) and the mixture was heated under reflux for 1 hour. The resulting sodium salt was filtered, dissolved in the minimum volume of hot water and poured into a solution of acetic acid (100 ml: 2N). The solution was cooled, the precipitated acid was collected, washed with cold water and dried. Recrystallization from dilute acetic acid gave 1-(2-carboxychromon-5-yloxy)-2-hydroxy-3-p-bromophenoxypropane (6.05 g) as white needles, m.p. 192°–194°C.

Analysis: Found: C, 49.98%; H, 3.85%; Br, 18.03%. $C_{19}H_{15}BrO_7 \cdot H_2O$ requires: C, 50.3%; H, 3.75%; Br, 17.67%.

EXAMPLE 8

1-(2-Carboxychromon-5-yloxy)-2-Hydroxy-3-p-Bromophenoxypropane Sodium Salt

A solution of sodium carbonate (0.1N; 100 ml) was added to 1-(2-carboxychromon-5-yloxy)-2-hydroxy-3-p-bromophenoxypropane (4.35 g). The suspension was heated on a water bath until the acid had dissolved completely and allowed to cool. The iridescent solid that separated was collected by centrifugation and washed with water (100 ml). The product was finally freeze-dried to give 1-(2-carboxychromon-5-yloxy)-2-hydroxy-3-bromophenoxypropane sodium salt (3.3 g), m.p. 254°–256°C.

Analysis: Found: C, 49.66%; H, 3.54%; Br, 17.30%. $C_{19}H_{14}BrO_7Na$ requires: C, 49.9%; H, 3.32%; Br, 17.5%.

EXAMPLE 9

1-(2-Acetyl-3-hydroxyphenoxy)-2-Hydroxy-3-p-Chlorophenoxypropane

A solution of 2,6-dihydroxyacetophenone (15.2 g) and p-chlorophenylglycidyl ether (18.45 g) in 2-ethoxyethanol (75 ml) containing benzyltrimethylammonium hydroxide solution (5 drops; 40%) was heated under reduced pressure and the residual viscous oil left to crystallize. The solid product was collected and washed with a small volume of diethyl ether to give 1-(2-acetyl-3-hydroxyphenoxy)-2-hydroxy-3-p-chlorophenoxypropane (21.0 g) as a pale yellow solid, m.p. 112.5°–114°.

Analysis: Found: C, 60.8%; H, 5.1%; Cl, 10.0%. $C_{17}H_{17}ClO_5$ requires: C, 60.7%; H, 5.1%; Cl, 9.5%.

EXAMPLE 10

1-(2-Carbethoxychromon-5-yloxy)-2-Hydroxy-3-p-Chlorophenoxypropane

A mixture of 1-(2-acetyl-3-hydroxyphenoxy)-2-hydroxy-3-p-chlorophenoxypropane (13.5 g) and diethyl oxalate (15 ml) was added to a suspension of alcohol-free sodium ethoxide (prepared from sodium 3 g) in absolute ether (200 ml). The mixture was heated under reflux for 1.5 hours during which time a yellow solid separated. The reaction mixture was poured onto ice (100 g) and acidified with a solution of acetic acid (12 ml) in water (80 ml). The ether layer was separated and the aqueous layer extracted with ether (3 × 25 ml). The ether layer was combined with the ether extracts and the solvent was evaporated. Acetic acid (80 ml) and hydrochloric acid (30 ml) were added to the residue and the resulting solution was heated under reflux for 1 hour. On pouring into water a beige gum was precipitated which soon solidified and was filtered. Recrystallization from acetic acid gave crude 1-(2-carboxychromon-5-yloxy)-2-hydroxy-3-p-chlorophenoxypropane (12.0 g), as a white solid, m.p. 191°–193°. The impure acid (10 g) was heated under reflux for 5 hours with ethanol (100 ml) and concentrated sulphuric acid (10 drops). The solvent was then removed on a rotary evaporator; the residual oil was dissolved in chloroform and washed successively with sodium bicarbonate solution and water. The solvent was removed and a small volume of ether was added to the residual oil which slowly crystallized to give a white solid (8.4 g), m.p. 98°–100°. Recrystallization from aqueous ethanol gave 1-(2-carboxychromon-5-yloxy)-2-hydroxy-3-p-chlorophenoxypropane (6.6 g) as white fluffy needles, m.p. 98°–100°C.

Analysis: Found: Cl, 8.46%. $C_{21}H_{19}ClO_7$ requires: Cl, 8.48%.

A white solid that separated while washing with sodium bicarbonate solution was filtered, washed with cold water and dried to give 1-(2-carboxychromon-5-yloxy)-2-hydroxy-3-p-chlorophenoxypropane sodium salt, (1.6 g). m.p. 242°C.

Analysis: Found: C, 54.04%; H, 3.76%; Cl, 8.82%. $C_{19}H_{14}ClO_7 \cdot 1/2 H_2O$ requires: C, 54.1%; H, 3.8%; Cl, 8.43%.

EXAMPLE 11

1-(2-Carboxychromon-5-yloxy)-2-Hydroxy-3-p-Chlorophenoxypropane

A solution of sodium hydroxide (0.6 g) in ethanol was added to 1-(2-carbethoxychromon-5-yloxy)-2-hydroxy-3-p-chlorophenoxypropane (6.28 g) and the mixture was heated under reflux for 1 hour. The resulting sodium salt was filtered, dissolved in the minimum volume of hot water and poured into a solution of acetic acid (100 ml, 2N). The solution was cooled, the precipitated acid was filtered, washed with cold water and dried. Recrystallization from dilute acetic acid gave 1-(2-carboxychromon-5-yloxy)-2-hydroxy-3-p-chlorophenoxypropane (6.0 g) as white needles, m.p. 193°–195°C.

Analysis: Found: C, 55.22%; H, 4.56%; Cl, 8.56%. $C_{19}H_{15}ClO_7 \cdot H_2O$ requires C, 55.7%; H, 4.16%; Cl, 8.68%.

EXAMPLE 12

1-(2-Acetyl-3-hydroxyphenoxy-2-Hydroxy-3-p-Methoxyphenoxypropane

A solution of 2,6-dihydroxyacetophenone (15.2g) and p-methoxyphenylglycidyl ether (18.0g) in 2-ethoxyethanol (75 ml) containing benzyltrimethylammonium hydroxide solution (5 drops: 40%) was heated under reflux for 48 hours. The solvent was then removed under reduced pressure and the residual viscous orange oil was allowed to stand overnight during which time crystallization occurred. The solid was triturated with ether, filtered and washed with a little ether to give 1-(2-acetyl-3-hydroxyphenoxy)-2-hydroxy-3-p-methoxyphenoxypropane (18.65 g) as a pale yellow solid, m.p. 100°–101.5°C.

Analysis: Found: C, 64.9%; H, 5.95%. $C_{18}H_{20}O_6$ requires: C, 65.1%; H, 6.0%.

EXAMPLE 13

1-(2-Carboxychromon-5-yloxy)-2-Hydroxy-3-p-Methoxyphenoxypropane

A mixture of 1-(2-acetyl-3-hydroxyphenoxy)-2-hydroxy-3-p-methoxyphenoxypropane (13.3 g) and diethyl oxalate (15 ml) was added to alcohol-free sodium ethoxide (prepared from sodium 3.0 g) in absolute ether (100 ml). The mixture was heated under reflux for 1.5 hours during which time a yellow solid separated. The residue was poured onto ice (100 g) and acidified with a solution of acetic acid (12 ml) in water (80 ml). The ether layer was separated and the aqueous solution was extracted with ether (3 × 25 ml). The combined ethereal layers were evaporated and the residue was dissolved in a mixture of acetic acid (80 ml) and hydrochloric acid (30 ml) and heated under reflux for 1 hour. On pouring into water (1 L) an off white solid was precipitated which was collected and recrystallized from acetic acid to give 1-(2-carboxychromon-5-yloxy)-2-hydroxy-3-p-methoxyphenoxypropane (12.0 g) as a white solid, m.p. 125°–126°C.

Analysis: Found: C, 59.12%; H, 4.94%. $C_{20}H_{18}O_8H_2O$ requires: C, 59.4%; H, 4.94%.

EXAMPLE 14

1-(2-Carbethoxychromon-5-yloxy)-2-Hydroxy-3-p-Methoxyphenoxypropane

A mixture of 1-(2-carboxychromon-5-yloxy)-2-hydroxy-3-p-methoxy-phenoxypropane (10.0 g), ethyl alcohol (5 ml) benzene (100 ml) and concentrated sulphuric acid (5 drops) was heated under a Dean and Stark phase separator for 20 hours. The cooled solution was washed with saturated sodium bicarbonate solution and then with water. Removal of the benzene under reduced pressure afforded a solid which was recrystallized from aqueous dioxane to give 1-(2-carbethoxychromon-5-yloxy)-2-hydroxy-3-p-methoxyphenoxypropane, m.p. 135°–136.5°C as white needles.

Analysis: Found: C, 63.95%; H, 5.38%. $C_{22}H_{22}O_8$ requires: C, 63.7%; H, 5.31%.

EXAMPLE 15

1-(2-Carboxychromon-5-yloxy)-2-Hydroxy-3-p-Methoxyphenoxypropane Sodium Salt

A solution of sodium hydroxide (0.6 g) in ethyl alcohol (100 ml) was added to 1-(2-carbethoxychromon-5-yloxy)-2-hydroxy-3-p-methoxyphenoxypropane (6.2 g) and the mixture was heated under reflux for 1 hour. The resulting solid was filtered and recrystallized from water to yield 1-(2-carboxychromon-5-yloxy)-2-hydroxy-3-p-methoxyphenoxypropane sodium salt (5 g) as a light beige solid m.p. 221°–223°C.

Analysis: Found: C, 56.56%; H, 4.42%. $C_{20}H_{17}O_8Na \cdot H_2O$ requires: C, 56.3%; H, 4.7%.

EXAMPLE 16

1-(2-Carboxychromon-5-yloxy)-2-Hydroxy-3-o-Cresyloxypropane

A solution of 2,6-dihydroxyacetophenone (15.2 g) and o-cresylglycidyl ether (16.4 g) in 2-ethoxyethanol (75 ml) containing benzyltrimethylammonium hydroxide solution (10 drops; 40%) was heated under reflux for 48 hours. Following removal of the 2-ethoxyethanol under reduced pressure, the resulting solid was washed with ether to give 1-(2-acetyl-3-hydroxyphenoxy)-2-hydroxy-3-o-cresyloxypropane (19.2 g) as a cream solid, m.p. 101°–102.5°C.

Analysis: Found: C, 68.1%; H, 6.3%. $C_{18}H_{20}O_5$ requires: C, 68.3%; H, 6.4%.

EXAMPLE 17

1-(2-Carboxychromon-5-yloxy)-2-Hydroxy-3-o-Cresyloxypropane

A solution of 1-(2-acetyl-3-hydroxyphenoxy)-2-hydroxy-3-o-cresyloxypropane (18.96 g) in diethyl oxalate (22.5 ml) was added to a suspension of sodium ethoxide, prepared from sodium (4.5 g) and ethyl alcohol (4.5 ml), in benzene (150 ml). The mixture was heated under reflux for 1.5 hours, cooled, and filtered after pouring into ether (150 ml). The residual solid was washed with ether and dried, and then added to a mixture of glacial acetic acid (120 ml) and concentrated hydrochloric acid (45 ml) and heated under reflux for 1 hour. After cooling, the residue was poured with stirring into cold water (1 L). The precipitated gum solidified after decanting the liquor and washing with water. The beige solid was recrystallized twice from ethyl acetate and finally from alcohol to give 1-(2-carboxy-chromon-5-yloxy)-2-hydroxy-3-o-cresyloxypropane (6.0g) as an off white solid, m.p. 95°–97°C.

Analysis: Found: C, 57.8%; H, 5.3%. $C_{20}H_{18}O_7 \cdot 5/2 H_2O$ requires: C, 57.8%; H, 5.5%.

EXAMPLE 18

1-(2-Carbethoxychromon-5-yloxy)-2-Hydroxy-3-o-Cresyloxypropane

A mixture of 1-(2-carboxychromon-5-yloxy)-2-hydroxy-3-o-cresyloxypropane (10.0 g), ethyl alcohol (5 ml), benzene (100 ml) and concentrated sulphuric acid (5 drops) were heated together under a Dean and Stark trap for 18 hours. After cooling, the solution was washed successively with sodium bicarbonate solution and water. Removal of the benzene afforded a viscous oil nucleated with crystals. Recrystallization of the crude product from aqueous dioxane gave 1-(2-carbethoxychromon-5-yloxy)-2-hydroxy-3-o-cresyloxypropane (8.75 g), m.p. 75°–76°C.

Analysis: Found: C, 63.75%; H, 6.00%. $C_{22}H_{22}O_7 \cdot H_2O$ requires: C, 63.4%; H, 5.77%.

EXAMPLE 19

1-(2-Carboxychromon-5-yloxy)-2-Hydroxy-3-o-Cresyloxypropane Sodium Salt

A solution of sodium hydroxide (0.8 g) in ethyl alcohol (100 ml) was added to 1-(2-carbethoxychromon-5-yloxy)-2-hydroxy-3-o-cresyloxypropane (7.96 g) and the mixture heated under reflux for 1 hour. The resulting solid was filtering and washed with a small volume of cold water to give 1-(2-carboxychromon-5-yloxy)-2- hydroxy-3-o-cresyloxypropane sodium salt (3.8 g), m.p. 228°–230°C.

Analysis: Found: C, 60.23%; H, 4.22%. $C_{20}H_{17}O_7Na$ requires: C, 61.2%; H, 4.33%.

EXAMPLE 20

1-(2-Acetyl-3-hydroxyphenoxy)-2-Hydroxy-3-p-t-Butylphenoxypropane

A solution of 2,6-dihydroxyacetophenone (15.2 g), p-t-butylphenylglycidyl ether (20.6 g) and benzyltrimethylammonium hydroxide (5 drops of a 40% solution) in 2-ethoxyethanol (75 ml) was heated under reflux for 48 hours. The solvent was removed under reduced pressure giving 1-(2-acetyl-3-hydroxyphenoxy)-2-hydroxy-3-p-t-butylphenoxypropane (38.85 g) as a viscous orange oil.

EXAMPLE 21

1-(2-Carboxychromon-5-yloxy)-2-Hydroxy-3-p-t-Butylphenoxypropane

A solution of 1-(2-acetyl-3-hydroxyphenoxy)-2-hydroxy-3-p-t-butylphenoxypropane (14.4 g) in diethyl oxalate (15 ml) was added to a suspension of sodium ethoxide, prepared from sodium (3.0 g) and ethanol (30 ml), in ether (200 ml). The mixture was heated under reflux for 1.5 hours, and the brown-coloured residue was poured onto ice (100 g). After acidification with a solution of acetic acid (12 ml) in water (80 ml), the ether layer was separated, and the aqueous solution extracted with ether (3 × 25 ml). The solvent was then removed from the combined ethereal layer and ethereal extracts. The residue was dissolved in a mixture of acetic acid (80 ml) and hydrochloric acid (30 ml) and heated under reflux for 1 hour. On pouring into water (1 L) 1-(2-carboxychromon-5-yloxy)-3-p-t-butylphenoxypropane, 10.7 g, was obtained as a beige gum.

EXAMPLE 22

1-(2-Carbethoxychromon-5-yloxy)-2-Hydroxy-3-p-t-Butylphenoxypropane 1-(2-carboxychromon-5-yloxy)-2-hydroxy-3-p-t-butylphenoxypropane (10.7 g), benzene (100 ml), ethanol (5 ml) and sulphuric acid (10 drops) were heated under reflux in a Dean and Stark separator until no more water passed over (about 6 hours). After cooling, the solution was washed with saturated sodium bicarbonate solution, and then water. The solvent was removed under reduced pressure to give a very viscous brown oil, from which solid material separated on standing. This solid was filtered off and washed several times with ether to give 1-(2-carbethoxy-chromon-5-yloxy)-2-hydroxy-3-p-t-butylphenoxypropane, 6.1 g, as a cream solid. A portion recrystallized from aqueous ethanol afforded almost colorless flakes m.p. 99°–101.5°.

Analysis: Found: C, 67.95%; H, 6.46%. $C_{25}H_{28}O_7$ requires: C, 68.17%; H, 6.41%.

EXAMPLE 23

1-(2-Carboxychromon-5-yloxy)-2-Hydroxy-3-p-t-Butylphenoxypropane Sodium Salt

A solution of sodium hydroxide (0.4 g) in ethanol (100 ml, 96%) was added to 1(2-carbethoxychromon-5-yloxy)-2-hydroxy-3-p-t-butylphenoxypropane (4.40 g) and the mixture warmed gently under reflux for 10 minutes. The cream solid was filtered off, washed with a little ethanol, and dried. It was then dissolved in water, charcoaled, filtered, and poured into dilute acetic acid. The sticky solid was filtered off, dissolved in acetone, and the acetone concentrated to give a yellow solid (3.5 g) m.p. 90°. This solid dissolved in sodium carbonate solution (0.1N, 85 ml) and the solution filtered and freeze-dried to give the sodium salt (3.9 g) as an off-white solid m.p. 230°–232°.

Analysis: Found: C, 57.42%; H, 5.55%. $C_{23}H_{23}O_7Na.2.5H_2O$ requires: C, 57.6%; H, 5.88%.

EXAMPLE 24

1-(2-Acetyl-3-hydroxyphenoxy)-2-Hydroxy-3-(2,6-dimethylphenoxy)propane

A solution of 2,6-dihydroxyacetophenone (15.2 g), 2,6-dimethylphenylglycidyl ether (17.8 g) and trimethylbenzylammonium hydroxide solution (10 drops of a 40% solution) in 2-ethoxyethanol (75 ml) was heated under reflux for 2 days. The solvent was then removed under reduced pressure and the residue allowed to stand for 2 days. The oily crystalline materials was then sucked dry on a filter pump and washed with the minimum volume of ether to give 1-(2-acetyl-3-hydroxyphenoxy)-2-hydroxy-3-(2,6-dimethyl-phenoxy) propane (12.7 g) as a pale primrose solid, m.p. 88°–90°. A portion was recrystallized from aqueous ethanol to give pale yellow prisms, m.p. 88°–90°C.

Analysis: Found: C, 68.83%; H, 6.62%. $C_{19}H_{22}O_5$ requires: C, 69.07%; H, 6.71%.

EXAMPLE 25

1-(2-Carbethoxychromon-5-yloxy)-2-Hydroxy-3-(2,6-dimethylphenoxy)propane

A solution of 1-(2-acetyl-3-hydroxyphenoxy)-2-hydroxy-3-(2,6-dimethylphenoxy) propane (12.7 g) in diethyl oxalate (15 ml) was added to a suspension of sodium ethoxide, prepared from sodium (3.0 g) and ethanol (30 ml), in ether (200 ml). The mixture was heated under reflux for 1.5 hours, and the resulting cherry-red solution poured onto ice (100 g), and acidified with a solution of acetic acid (12 ml) in water (80 ml). The ether layer was separated, and the aqueous layer extracted with ether (3 × 25 ml), adding the extracts to the organic layer. The solvent was then removed and the residue dissolved in absolute ethanol (100 ml) to which hydrochloric acid (5 drops) was added. The yellow solution was heated under reflux for 0.5 hours and the solvent removed to give 1-(2-carbethoxychromon-5-yloxy)-2-hydroxy-3-(2,6-dimethyl)-phenoxypropane as a viscous yellow oil (15.9 g).

EXAMPLE 26

1-(2-Carboxychromon-5-yloxy)-2-Hydroxy-3-(2,6-dimethylphenoxy)propane Sodium Salt A solution of sodium hydroxide (1.6 g) in ethanol (100 ml) was added to a solution of 1-(2-carbethoxychromon-5-yloxy)-2-hydroxy-3-(2,6-dimethylphenoxy) propane (15.9 g) in ethanol (100 ml) at room temperature. The mixture was then heated under reflux on a water bath for 30 minutes, allowed to cool, and the white precipitate filtered off, washed with ethanol, and dried. The residue was dissolved in water, charcoaled, filtered, and the solution freeze-dried to give the sodium salt (12.0 g) as an off-white solid m.p. 228°–230°.

EXAMPLE 27

1-(2-Acetyl-3-hydroxyphenoxy)-2-Hydroxy-3-m-Cresyloxypropane

A solution of 2,6-dihydroxyacetophenone (15.2 g), m-cresylglycidyl ether (16.4 g) and benzyltrimethylammonium hydroxide (10 drops of a 40% solution) in 2-ethoxyethanol (75 ml) was heated under reflux for 48 hours. The solvent was then removed under reduced pressure to give 1-(2-acetyl-3-hydroxyphenoxy)-2-hydroxy-3-m-cresyloxypropane (31.5 g) as a viscous amber oil.

EXAMPLE 28

1-(2-Carbethoxychromon-5-yloxy)-2-Hydroxy-3-m-Cresyloxypropane

A solution of 1-(2-acetyl-3-hydroxyphenoxy)-2-hydroxy-3-m-cresyloxypropane (25.3 g) in diethyl oxalate (30 ml) was added to a suspension of sodium ethoxide, prepared from sodium (6.0 g) and ethanol (60 ml), in dry ether (400 ml). The mixture was heated under reflux for 1.5 hours; the brown residue was poured onto ice (200 g) and acidified with a solution of acetic acid (24 ml) in water (160 ml). The ether layer was separated after adding more water (200 ml) and the aqueous layer extracted with ether (3 × 50 ml), adding the extracts to the organic layer. The solvent was then removed and the residue dissolved in absolute ethanol (200 ml) to which hydrochloric acid (10 drops) was added. The solution was heated under reflux for 30 minutes and the solvent removed to give a viscous brown oil, which solidified on standing. The oily crystals were filtered off and after recrystallization from aqueous ethanol gave 1-(2-carbethoxy-chromon-5-yloxy)-2-hydroxy-3-m-cresyloxypropane (8.2 g) as a white solid, m.p. 72°–74°.

Analysis: Found: C, 62.55%; H, 5.80%. $C_{22}H_{22}O_7 \cdot 1.5H_2O$ requires: C, 62.2%; H, 5.92%.

EXAMPLE 29

1-(2-Carboxychromon-5-yloxy)-2-Hydroxy-3-m-Cresyloxypropane Sodium Salt

A solution of sodium hydroxide (0.8 g) in ethanol (50 ml, 96%) was added to a solution of 1-(2-carbethoxychromon-5-yloxy)-2-hydroxy-3-m-cresyloxypropane (7.96 g) in ethanol (50 ml, 96%) at room temperature. The mixture was then heated under reflux on a water bath for 1 hour, allowed to cool, and the ethanol removed by evaporation to give a yellow solid. This was dissolved in hot water, charcoaled, filtered, and freeze-dried to yield the sodium salt (7.5 g) as a white solid, m.p. 225°.

Analysis: Found: C, 57.35%; H, 5.24%. $C_{21}H_{19}O_7Na \cdot 2H_2O$ requires: C, 57.1%; H, 5.24%.

EXAMPLE 30

1-(2-Acetyl-3-hydroxyphenoxy)-2-Hydroxy-3-p-Ethylphenoxypropane

A solution of 2,6-dihydroxyacetophenone (15.2 g), p-ethylphenylglycidyl ether (17.8 g) and benzyltrimethylammonium hydroxide (5 drops of a 40% solution) was heated under reflux for 3 days. The solvent was removed under reduced pressure affording 1-(2-acetyl-3-hydroxyphenoxy)-2-hydroxy-3-p-ethylphenoxypropane, 33.0 g, as a cherry-red oil.

EXAMPLE 31

1-(2-Carbethoxychromon-5-yloxy)-2-Hydroxy-3-p-Ethylphenoxypropane

A solution of 1-(2-acetyl-3-hydroxyphenoxy)-2-hydroxy-3-p-ethylphenoxypropane (25.6 g) in diethyl oxalate (30 ml) was added to a suspension of sodium ethoxide, prepared from sodium (6.0 g) and ethanol (60 ml), in dry ether (400 ml). The mixture was heated under reflux for 1.5 hours and the greenish-brown residue was poured onto ice (200 g) and acidified with a solution of acetic acid (24 ml) in water (160 ml). The ether layer was separated after the addition of a further quantity of water (200 ml), and the aqueous layer was extracted with ether (3 × 50 ml), adding the extracts to the organic layer. The solvent was then removed and the residue dissolved in absolute ethanol (200 ml) to which hydrochloric acid (10 drops) was added. The solution was heated under reflux for 1 hour and the solvent was then removed to give a brownish oil from which crystals separated on standing overnight. These were filtered off, and washed with the minimum volume of ether to afford 1-(2-carbethoxy-chromon-5-yloxy)-2-hydroxy-3-p-ethylphenoxypropane (15.7 g) as a white solid, m.p. 80°–85°. A portion was recrystallized from aqueous ethanol to give white flakes, m.p. 84°–86°.

Analysis: Found: C, 64.58%; H, 6.19%. $C_{23}H_{24}O_7 \cdot H_2O$ requires: C, 64.17%; H, 6.09%.

EXAMPLE 32

1-(2-Carboxychromon-5-yloxy)-2-Hydroxy-3-p-Ethylphenoxypropane Sodium Salt

A solution of sodium hydroxide (1.2 g) in ethanol (75 ml, 96%) was added to a solution of 1-(2-carbethoxychromon-5-yloxy)-2-hydroxy-3-p-ethylphenoxypropane (12.4 g) in ethanol (100 ml, 96%) at room temperature. The mixture was then heated under reflux on a water bath for 30 minutes, allowed to cool, and the solid filtered off, washed with ethanol, and dried. It was then recrystallized from water, and finally redissolved in water, filtered and freeze-dried to give the sodium salt (5.9 g) as a silvery-white solid, m.p. 235°.

Analysis: Found: C, 62.07%; H, 4.94%. $C_{21}H_{19}O_7Na$ requires: C, 62.07%; H, 4.71%.

EXAMPLE 33

1-(2-Acetyl-3-hydroxyphenoxy)-2-Hydroxy-3-p-Cyanophenoxypropane

A solution of 2,6-dihydroxyacetophenone (15.2 g), p-cyanophenylglycidyl ether (17.5 g) and benzyltrimethylammonium hydroxide (10 drops of a 40% solution) was heated under reflux for 2 days. The solvent was then removed by evaporation under reduced pressure to give 1-(2-acetyl-3-hydroxyphenoxy)-2-hydroxy-3-p-cyanophenoxypropane, 28.4 g, as a beige solid. A portion was recrystallized from ethanol affording cream prisms m.p. 157°–158°.

Analysis: Found: C, 65.95%; H, 5.11%; N, 4.23%. $C_{18}H_{17}NO_5$ requires: C, 66.05%; H, 5.24%; N, 4.28%.

EXAMPLE 34

1-(2-Carbethoxychromon-5-yloxy)-2-Hydroxy-3-p-Cyanophenoxypropane

A suspension of 1-(2-acetyl-3-hydroxyphenoxy)-2-hydroxy-3-p-cyanophenoxypropane (13.1 g) in diethyl oxalate (15 ml) was added to a suspension of sodium ethoxide, prepared from sodium (3.0 g) and ethanol (30 ml) in dry benzene (200 ml). The resulting mixture was heated under reflux for 2 hours, cooled, poured onto ice (100 g), and acidified with a solution of acetic acid (12 ml) in water (80 ml). The benzene layer was separated, and the aqueous layer extracted with ether (3 × 25 ml). The extracts were combined with the organic layer, the solvent was removed, and the residue was dissolved in absolute ethanol (100 ml) to which hydrochloric acid (5 drops) was added. The yellow solution was heated under reflux for 1 hour and the solvent removed to give a yellow solid. Recrystallization from ethanol gave 1-(2-carbethoxychromon-5-yloxy)-2-hydroxy-3-p-cyanophenoxypropane (5.4 g) as a beige solid m.p. 137°–139° C.

EXAMPLE 35

1-(2-Carboxychromon-5-yloxy)-2-Hydroxy-3-p-Cyanophenoxypropane Sodium Salt

A solution of sodium hydroxide (0.4 g) in ethanol (50 ml) was added to a solution of 1-(2-carbethoxychromon-5-yloxy)-2-hydroxy-3-p-cyanophenoxypropane (4.1 g) in ethanol (100 ml). The resulting suspension was heated under reflux on a water bath for 1 hour, allowed to cool, and the precipitate filtered off, washed with ethanol, and dried. It was then dissolved in water, the solution treated with charcoal, filtered, and freeze-dried to give the sodium salt (2.1 g) as a pale beige solid, m.p. 180°–185° C.

Analysis: Found: C, 49.82%; H, 4.59%; N, 2.60%. $C_{20}H_{14}NO_7Na.4H_2O$ requires: C, 50.6%; H, 4.67%; N, 2.95%.

EXAMPLE 36

1-(2-Acetyl-3-hydroxyphenoxy)-2-Hydroxy-3-p-Nitrophenoxypropane

A solution of 2,6-dihydroxyacetophenone (15.2 g) p-nitrophenyl-glycidyl ether (19.5 g) and benzyltrimethylammonium hydroxide (10 drops of a 40% solution) in 2-ethoxyethanol (75 ml) was heated under reflux for 3 days. The solvent was removed under reduced pressure and the resulting beige solid triturated with ether, filtered off and dried to give 1-(2-acetyl-3-hydroxyphenoxy)-2-hydroxy-3-p-nitrophenoxypropane (23.0 g). A portion was recrystallized from ethanol to give beige prisms m.p. 143°–145°.

Analysis: Found: C, 59.03%; H, 4.88%; N, 4.00%. $C_{17}H_{17}NO_{17}$ requires: C, 58.79%; H, 4.93%; N, 4.03%.

EXAMPLE 37

1-(2-Carbethoxychromon-5-yloxy)-2-Hydroxy-3-p-Nitrophenoxypropane

A solution of 1-(2-acetyl-3-hydroxyphenoxy)-2-hydroxy-3-p-nitrophenoxypropane (20.82 g) in diethyl oxalate (22.5 ml) was added to a suspension of sodium ethoxide, prepared from sodium (4.5 g) and ethanol (45 ml), in dry ether (300 ml). The resulting yellow suspension was heated under reflux for 2.5 hours, then poured onto ice (150 g) and acidified with a solution of acetic acid (24 ml) in water (160 ml). The two-phase mixture, after filtering to remove starting material (6.0 g) and washing with a little ether, was separated. The aqueous layer was extracted with ether (4 × 50 ml), and the extracts added to the organic layer. The solvent was then removed and the residue dissolved in absolute ethanol (100 ml) to which hydrochloric acid (5 drops) was added. The solution was heated under reflux for 1 hour, and the solvent was then removed to give a brownish-yellow oily solid. This was triturated with ether to give 1-(2-carbethoxy-chromon-5-yloxy-3-p-nitrophenoxypropane (12.0 g) as a yellow solid. A portion was recrystallized from ethanol to give yellow prisms m.p. 154°–156°.

Analysis: Found: C, 58.56%; H, 4.43%; N, 3.23%. $C_{21}H_{19}NO_9$ requires: C, 58.74%; H, 4.46%; N, 3.26%.

EXAMPLE 38

1-(2-Carboxychromon-5-yloxy)-2-Hydroxy-3-p-Nitrophenoxypropane Sodium Salt

A solution of sodium hydroxide (0.8 g) in ethanol (50 ml) was added to a suspension of 1-(2-carbethoxychromon-5-yloxy)-2-hydroxy-3-p-nitrophenoxypropane (8.58 g) in ethanol (100 ml) at room temperature. The mixture was heated under reflux for 2 hours and the alcohol then removed under reduced pressure. The product was dissolved in hot water, charcoaled, filtered and allowed to crystallize. The white solid was filtered off, washed with a little water, redissolved in hot water, filtered and freeze-dried to give the sodium salt (4.0 g) as a white solid, m.p. 224°–226°.

Analysis: Found: C, 49.93%; H, 3.64%; N, 3.06%. $C_{19}H_{14}NO_9Na.2H_2O$ requires: C, 49.70%; H, 3.95%; N, 3.05 %.

EXAMPLE 39

1-(4-Acetyl-3-hydroxyphenoxy)-2-Hydroxy-3-Phenoxypropane

A solution of resacetophenone (15.2 g), phenylglycidyl ether (15.0 g) and benzyltrimethylammonium hydroxide (5 drops of a 40% solution) in 2-ethoxyethanol (75 ml) was heated under reflux for 2 days. Removal of solvent under reduced pressure yielded a dark, viscous oil, which was allowed to stand for 48 hours, by which time it had crystallized to a solid mass. This was triturated with a mixture of ether and light petroleum (b.p. 40°–60°.), filtered, washed with a little more ether-petroleum and dried. Crystallization from methanol gave 1-(4-acetyl-3-hydroxyphenoxy)-2-hydroxy-3-phenoxypropane as a greyish-white solid, 9.0 g, m.p. 63°–65°.

Analysis: Found: C, 67.2%; H, 6.0%. $C_{17}H_{18}O_5$ requires: C, 67.5%; H, 6.0%.

EXAMPLE 40

1-(2-Carboxychromon-7-yloxy)-2-Hydroxy-3-Phenoxypropane

A solution of 1-(4-acetyl-3-hydroxyphenoxy)-2-hydroxy-3-phenoxy-propane (6.04 g) in diethyl oxalate (15 ml) was added to a suspension of sodium ethoxide, prepared from sodium (3.0 g) and ethanol (30 ml), in benzene (50 ml). The mixture was heated under reflux for 1.5 hours, then cooled and filtered. The residual yellow sodium salt was washed with ether, dried, and dissolved in a mixture of glacial acetic acid (80 ml) and concentrated hydrochloric acid (30 ml). This solution was heated under reflux for 1 hour, cooled, and poured with stirring into cold water (500 ml). The precipitated solid (6.0 g) was filtered off and crystallized from methanol to give 1-(2-carboxychromon-7-yloxy-3-phenoxypropane (4.3 g) as an off-white solid, m.p. 222°–223.5°.

Analysis: Found: C, 63.3%; H, 4.5%. $C_{19}H_{16}O_7$ requires: C, 64.1%; H, 4.5%.

EXAMPLE 41

1-(2-Carboxychromon-7-yloxy)-2-Hydroxy-3-Phenoxypropane Sodium Salt

Sodium carbonate solution (0.1N; 100 ml) was added to 1-(2-carboxy-chromon-7-yloxy)-2-hydroxy-3-phenoxypropane (3.56 g) and the mixture warmed on the water-bath until all the solid had dissolved. The solution was charcoaled, filtered and freeze-dried to give the sodium salt (4.1 g) as a white solid m.p. 235°–240°.

Analysis: Found: C, 57.29%; H, 4.34%. $C_{19}H_{15}O_7Na \cdot H_2O$ requires: C, 57.58%; H, 4.33%.

EXAMPLE 42

1-(2-Acetyl-3-hydroxyphenoxy)-2-Hydroxy-3-p-Carbethoxyphenoxypropane

A solution of 2,6-dihydroxyacetophenone (15.2 g), 4-carbethoxyphenylglycidyl ether (22.2 g) and benzyltrimethylammonium hydroxide (10 drops of a 40% solution) in 2-ethoxyethanol (75 ml) was heated under reflux for 48 hours. The solvent was then removed under reduced pressure, and the residual solid was triturated with ether to give a yellow powder (23.0 g). Recrystallization from aqueous ethanol yielded 1-(2-Acetyl-3-hydroxyphenoxy)-2-hydroxy-3-p-carbethoxyphenoxypropane as pale yellow needles, m.p. 104°–105.5° C.

Analysis: Found: C, 64.26%; H, 6.04%. $C_{20}H_{22}O_7$ requires: C, 64.16; H, 5.92%.

EXAMPLE 43

1-(2-Carbethoxychromon-5-yloxy)-2-Hydroxy-3-p-Carbethoxyphenoxypropane

To a suspension of sodium ethoxide, prepared from sodium (3.0 g) and ethanol (30 ml) in dry ether (200 ml), was added a solution of 1-(2-acetyl-3-hydroxyphenoxy)-2-hydroxy-3-p-carbethoxyphenoxypropane (15.0 g) in diethyl oxalate (15 ml). The mixture was heated under reflux for 2 hours, and then poured onto ice (100 g). After acidification with a solution of acetic acid (12 ml) in water (80 ml), the ether layer was separated and the aqueous layer extracted with ether (3 × 25 ml). The combined ethereal extracts were evaporated under reduced pressure to give an orange oil. This was dissolved in ethanol (96%, 100 ml) containing hydrochloric acid (5 drops) and the solution was heated under reflux for 1 hour. The ethanol was then removed under reduced pressure to yield a beige solid (18.65 g). Crystallization from ethanol gave 1-(2-carbethoxy-chromon-5-yloxy)-2-hydroxy-3-p-carbethoxyphenoxypropane as white prisms m.p. 133.5°–135° C.

Analysis: Found: C, 63.37%; H, 5.17%. $C_{24}H_{24}O_9$ requires: C, 63.15%; H, 5.30%.

EXAMPLE 44

1-(2-Carboxychromon-5-yloxy)-2-Hydroxy-3-p-Carbethoxyphenoxypropane Sodium Salt

A solution of sodium hydroxide (1.6 g) in ethanol (50 ml, 96%) was added to a solution of 1-(2-carbethoxychromon-5-yloxy)-2-hydroxy-3-p-carbethoxyphenoxypropane (9.13 g) in ethanol (100 ml, 96%). The suspension was heated under reflux for 2 hours and the ethanol was then removed under reduced pressure. The residue was dissolved in hot water, charcoaled, and the solution filtered and allowed to cool. 1-(2-Carboxychromon-5-yloxy)-2-hydroxy-3-p-carbethoxyphenoxypropane sodium salt (1.5 g) was precipitated as a white solid m.p. 215°–220°.

Analysis: Found: C, 58.19%; H, 4.00%. $C_{22}H_{19}O_9Na$ requires: C, 58.7%; H, 4.26%.

EXAMPLE 45

1-(2-Acetyl-3-hydroxyphenoxy)-2-Hydroxy-3-(2,5-dimethylphenoxy)propane

A solution of 2,6-dihydroxyacetophenone (15.2 g), 2,5-dimethylphenylglycidyl ether (17.8 g) and benzyltrimethylammonium hydroxide (10 drops of a 40% solution) in 2-ethoxyethanol (75 ml) was heated under reflux for 2 days. The solvent was then removed under reduced pressure to give a dark viscous oil which soon crystallized. The sticky solid was triturated with ether, filtered, and washed with small portions of ether to give 1-(2-acetyl-3-hydroxyphenoxy)-2-hydroxy-3-(2,5-dimethylphenoxy) propane (15.6 g) as a cream powder, m.p. 104°–105.5° C.

Analysis: Found: C, 68.72%; H, 6.51%. $C_{19}H_{22}O_5$ requires: C, 69.07%; H, 6.71%.

EXAMPLE 46

1-(2-Carbethoxychromon-5-yloxy)-2-Hydroxy-3-(2,5-dimethylphenoxy)propane

To a suspension of sodium ethoxide, prepared from sodium (3.0 g) and ethanol (30 ml), in dry ether (200 ml), was added a solution of 1-(2-acetyl-3-hydroxyphenoxy)-2-hydroxy-3-(2,5-dimethylphenoxy) propane (13.2 g) in diethyl oxalate (15 ml). The resultant solution was heated under reflux for 2 hours, and then poured onto ice (100 g). After acidification with a solution of acetic acid (12 ml) in water (80 ml), the ether layer was separated, and the aqueous layer extracted with ether (3 × 25 ml). The combined ethereal extracts were evaporated under reduced pressure to give a yellow oil. This was dissolved in ethanol (96%, 100 ml) containing hydrochloric acid (10 drops) and heated under reflux for 1 hour. Removal of the ethanol under reduced pressure gave 1-(2-carbethoxychromon-5-yloxy)-2-hydroxy-3-(2,5-dimethylphenoxy) propane as a yellow gum (15.2 g) which could not be crystallized.

EXAMPLE 47

1-2-Carboxychromon-5-yloxy)-2-Hydroxy--dimethylphenoxy) propane -(2,5-dimethyl- Sodium Salt.

A solution of sodium hydroxide (1.2 g) in ethanol (96%, 50 ml) was added to a solution of 1-(2-carbethoxychromon-5-yloxy)-2-hydroxy-3-(2,5-dimethylphenoxy) propane (12.4 g) in ethanol (96%, 50 ml). The resulting suspension was warmed under reflux for 1 hour, cooled, and the precipitate filtered off, washed with a little ethanol, and dried. It was then dissolved in hot water and the solution was charcoaled, filtered and freeze-dried to give 1-(2-carboxychromon-5-yloxy)-2-hydroxy-3-(2,5-dimethylphenoxy) propane sodium salt (8.5 g) as a white solid m.p. 228°–230°C.

Analysis: Found: C, 60.42%; H, 5.01%. $C_{19}H_{19}O_7Na \cdot 1/2H_2O$ requires: C, 60.71%; H, 4.85%.

EXAMPLE 48

1-(2-Acetyl-3-hydroxyphenoxy)-2-Hydroxy-3-(2-n-propylphenoxy)propane.

A solution of 2,6-dihydroxyacetophenone (15.2 g) 2-n-propylphenylglycidyl ether (19.2 g) and benzyltrimethylammonium hydroxide (10 drops of a 40% solution) in 2-ethoxyethanol (75 ml) was heated under reflux for 48 hours. The solvent was then removed under reduced pressure to give a dark oil which soon crystallized. The sticky residue was triturated with ether, filtered, and washed successively with small portions of ether to give 1-(2-acetyl-3-hydroxyphenoxy)-2-hydroxy-3-(2-n-propylphenoxy) propane (17.8 g) as a primrose powder m.p. 85°–86.5°C.

Analysis: Found: C, 69.41%; H, 6.82%. $C_{20}H_{24}O_5$ requires: C, 69.75%; H, 7.02%.

EXAMPLE 49

1-(2-Carbethoxychromon-5-yloxy)-2-Hydroxy-3-(2-n-propylphenoxy propane

To a suspension of sodium ethoxide, prepared from sodium (3.0 g) and ethanol (30 ml) in dry ether (200 ml), was added a solution of 1-(2-acetyl-3-hydroxphenoxy)-2-hydroxy-3-(2n-propylphenoxy) propane (13.8 g) in diethyl oxalate (15 ml). The resulting solution was heated under reflux for 2 hours then cooled and poured onto ice (100 g). After acidication with a solution of acetic acid (12 ml) in water (80 ml), the ether layer was separated and the aqueous layer was extracted with ether (3 × 25 ml). The combined organic extracts were evaporated under reduced pressure, then dissolved in a mixture of ethanol (100 ml) and hydrochloric acid (10 drops). This solution was heated under reflux for 1 hour. After removal of solvent under reduced pressure, 1-(2-carbethoxychromon-5-yloxy)-2-hydroxy-3-(2-n-propylphenoxy) propane (19.0 g) remained as a viscous yellow oil which could not solidified.

EXAMPLE 50

1-(2-Carboxychromon-5-yloxy)-2-Hydroxy-3-(2-n-propylphenoxy) propane Sodium Salt A solution of sodium hydroxide (1.2 g) in ethanol (96%, 50 ml) was added to a solution of 1-(2-carbethoxychromon-5-yloxy)-2-hydroxy-3-(2-n-propylphenoxy) propane (12.8 g) in ethanol (96%, 50 ml). The resulting suspension was heated under reflux for 1 hour, cooled, the solid filtered off, washed with ethanol, and dried. It was then dissolved in hot water, and the solution charcoaled, filtered and freeze-dried to yield 1-(2-carboxychromon-5-yloxy)-2-hydroxy-3-(2-n-propylphenoxy) propane sodium salt (8.3 g) as a white solid, m.p. 226°–228°C.

Analysis: Found: C, 60.18%; H, 5.18%. $C_{22}H_{21}O_7.Na.H_2O$ requires: C, 60.26%; H, 5.29%.

EXAMPLE 51

1-(4-Acetyl-3-hydroxphenoxy)-2-Hydroxy-3-p-Cyanophenoxypropane.

A solution of 2,4-dihydroxyacetophenone (15.2 g), p-cyano-phenylglycidyl ether (17.5 g) and benzyltrimethyl-ammonium hydroxide (10 drops of a 40% solution) in 2-ethoxyethanol (75 ml) was heated under relux for 48 hours. The solvent was then removed under reduced pressure to give a beige solid. This was triturated with a little ether and filtered to give a pale beige powder, (28.6 g). Recrystallization from ethanol yielded 1-(4-acetyl-3-hydroxy-phenoxy)-2-hydroxy-3-(p-cyanophenoxy) propane as white needles, m.p. 161.5°–163°C.

Analysis: Found: C, 66.22%; H, 5.16%; N, 4.14%. $C_{18}H_{17}NO_5$ requires C, 66.05%; H, 5.24%; N, 4.28%.

EXAMPLE 52

1-(2-Carbethoxychromon-7-yloxy)-2-Hydroxy-3-(p-cyanophenoxy) propane.

To a suspension of sodium ethoxide, prepared from sodium (6.0 g) and ethanol (60 ml) in dry ether (400 ml) was added a solution of 1-(4-acetyl-3-hydroxyphenoxy)-2-hydroxy-3-(p-cyanophenoxy) propane (26.2 g) and diethel oxalate (30 ml) in dimethyl sulphoxide (100 ml). After heating under reflux for 2 hours, the suspension was poured onto ice (200 g), acidified with a solution of acetic acid (24 ml) in water (160 ml), and the ether layer separated. The aqueous layer was extracted with ether (3 × 50 ml) and the combined ethereal extracts were evaporated under reduced pressure. The residue was dissolved in ethanol (200 ml) containing concentrated hydrochloric acid (20 drops) and the solution heated under reflux for 1 hour. Removal of the ethanol under reduced pressure gave a solid (24.6 g). On crystallization from ethanol 1-(2-carbethoxychromon-7-yloxy)-2-hydroxy-3-(p-cyanophenoxy) propane was obtained as white crystals m.p. 170°–172°C.

Analysis: Found: C, 64.75%; H, 4.80%; N, 3.46%. $C_{22}H_{19}NO_7$ requires: C, 64.54%; H, 4.68%; N, 3.42%.

EXAMPLE 53

1-(2-Carboxychromon-7-yloxy)-2-Hydroxy-3-(p-cyanophenoxy) propane Sodium Salt

A solution of sodium hydroxide (1.6 g) in ethanol (96%, 50 ml) was added to a solution of 1-(2-carbethoxychromon-7-yloxy)-2-hydroxy-3-(p-cyanophenoxy) propane (16.1 g) in ethanol (96%, 100 ml). The resulting suspension was heated under reflux for 1 hour, cooled, filtered, and the beige precipitate washed with a little ethanol and dried. It was then dissolved in hot water, the solution charcoaled, filtered and freeze-dried to give 1-(2-carboxy-chromon-7-yloxy)-2-hydroxy-3-(p-cyanophenoxy) propane sodium salt (10.7 g) as a beige powder m.p. 210°–215°C.

Analysis: Found: C, 56.88%; H, 3.53%; N, 3.15%. $C_{20}H_{14}NO_7Na.H_2O$ requires: C, 57.02%; H, 3.83%; N, 3.33%.

EXAMPLE 54

1-(3-Acetyl-4-hydroxphenoxy)-2-Hydroxy-3-(4-cyanophenoxy) propane.

A solution of 2,5-dihydroxyacetophenone (30.4 g), p-cyanophenylglycidyl ether (35.0 g) and benzyltrimethylammonium hydroxide (10 drops of a 40% solution) in 2-ethoxyethanol (150 ml) was heated under reflux for 72 hours. The solvent was then removed under reduced pressure to give a dark viscous oil which rapidly solidified. This solid was extracted with ether in a Soxhlet thimble and the ether then removed to give a yellow solid residue. This was triturated with a little ethanol, filtered off, washed with a little more ethanol and dried. Some further material was obtained by grinding the residue from the Soxhlet thimble and extracting it with boiling ether. Recrystallization from aqueous ethanol gave 1-(3-acetyl-4-hydroxyphenoxy)-2-hydroxy-3-(p-cyano-phenoxy) propane as lemon-yellow needles m.p. 118°–120°C.

Analysis: Found: C, 66.01%; H, 5.20%; N, 4.19%. $C_{18}H_{17}NO_5$ requires: C, 66.05%; H, 5.24%; N, 4.28%.

EXAMPLE 55

1-(2-Carbethoxychromon-6-yloxy)-2-Hydroxy-3-(p-cyanophenoxy) propane.

To a suspensioin of sodium ethoxide, prepared from sodium (6.0 g) and ethanol (60 ml) in dry ether (400 ml) and dimethyl sulphoxide (50 ml), was added a suspension of 1-(3-acetyl-4-hydroxyphenoxy-2-hydroxy-3-(p-cyanophenoxy) propane (26.2 g) in diethyl oxalate (30 ml). The resulting suspension was heated under reflux for 2 hours, cooled, and poured onto ice (200 g). After acidification with a solution of acetic acid (24 ml) in water (160 ml), the ether layer was separated, and the aqueous layer extracted with ether (3 × 50 ml). The combined organic extracts were evaporated under reduced pressure to give a yellow solid. This was dissolved in ethanol (200 ml) containing hydrochloric acid (20 drops) and the solution heated under reflux for 1 hour. After cooling, the beige solid (20.0 g) was filtered off. Recrystallization from aqueous dioxane gave 1-(2-carbethoxychromon-6-yloxy)-2-hydroxy-3-(p-cyanophenoxy) propane (17.3 g) as pale yellow crystals, m.p. 150°–152°C.

A portion was again crystallized from ethanol to give cream crystals m.p. 151°–152.5°C.

Analysis: Found: C, 64.34%; H, 4.52%; N, 3.31%. $C_{22}H_{19}NO_7$ requires: C, 64.54%; H, 4.68%; N, 3.42%.

EXAMPLE 56

1-(2-Carboxychromon-6-yloxy)-2-Hydroxy-3-(p-cyanophenoxy) propane Sodium Salt

A solution of sodium hydroxide (1.6 g) in ethanol (50 ml) was added to a solution of 1-(2-carboxychromon-6-yloxy)-2-hydroxy-3-(p-cyanophenoxy) propane (16.1 g) in ethanol (100 ml). The resulting suspension was heated under reflux for 1 hour, cooled, filtered, and the solid washed with a little ethanol and dried. It was then dissolved in water, the solution charcoaled, filtered and freeze-dried to give 1-(2-carboxychromon-6-yloxy)-2-hydroxy-3-(p-cyanophenoxy) propane sodium salt (16.5 g) as a pale yellow solid m.p. 285°–290° C.

Analysis: Found: C, 57.15%; H, 3.60%; N, 3.23%. $C_{20}H_{14}NO_7Na.H_2O$ requires: C, 57.02%; H, 3.83%; N, 3.33%.

EXAMPLE 57

1-(2-Acetyl-3-hydroxphenoxy)-2-Hydroxy-3-(m-trifluoromethylphenoxy) propane.

A solution of 2,6-dihydroxyacetophenone (30.4 g), m-trifluoromethylphenylglycidyl ether (43.6 g) and benzyltrimethylammonium hydroxide (20 drops of a 40% solution) in 2-ethoxyethanol (150 ml) was heated under reflux for 48 hours. The solvent was then removed by evaporation under reduced pressure to give a yellow residue. This was triturated with ether, filtered off and washed with ether to give a yellow solid (52.0 g). Crystallization from ethanol gave 1-(2-acetyl-3-hydroxphenoxy)-2-hydroxy-3-(m-trifluoromethylphenoxy) propane as cream needles m.p. 110°–112° C.

Analysis: Found: C, 58.55%; H, 4.82%; F 15.18%. $C_{18}H_{17}F_3O_5$ requires: C, 58.3%; H, 4.63%; F, 15.4%.

EXAMPLE 58

1-(2-Carbethoxychromon-5-yloxy)-2-Hydroxy-3-(m-trifluoromethylphenoxy) propane.

A suspension of 1-(2-acetyl-3-hydroxyphenoxy)-2-hydroxy-3-(m-trifluoromethylphenoxy) propane (29.6 g) in diethyl oxalate (30 ml) was added to a suspension of sodium ethoxide, prepared from sodium (6.0 g) and ethanol (60 ml) in dry ether (400 ml). The resulting solution was heated under reflux for 2 hours, cooled, and poured onto ice (200 g). After acidification with a solution of acetic acid (24 ml) in water (160 ml), the ether layer was separated, and the aqueous layer extracted with ether (3 × 50 ml). The combined extracts were evaporated under reduced pressure, and the residue dissolved in ethanol (96%, 100 ml) to which hydrochloric acid (20 drops) was added. This solution was heated under reflux for 1 hour, and the ethanol then removed under reduced pressure to give a beige solid, which was crystallized from aqueous ethanol to yield 1-(2-carbethoxychromon-5-yloxy)-2-hydroxy-3-(m-trifluoromethylphenoxy) propane (19.5 g) as white needles m.p. 70°– 75° C.

Analysis: Found: C, 55.62%; H, 4.08%; F, 11.76%. $C_{22}H_{19}F_3O_7.H_2O$ requires: C, 56.2%; H, 4.51%; F, 12.1%.

EXAMPLE 59

1-(2-Carboxychromon-5-yloxy)-2-Hydroxy-2-(m-trifluoromethylphenoxy) propane Sodium Salt A solution of sodium hydroxide (1.6 g) in ethanol (96%, 50 ml) was added slowly with stirring to a hot solution of 1-(2-carbethoxychromon-5-yloxy)-2-hydroxy-3-(m-trifluoromethylphenoxy) propane (18.1 g) in ethanol (96%, 100 ml. The resulting mixture was heated under reflux for 1 hour, cooled, and the precipitated solid filtered off, washed with ethanol and dried. It was then crystallized from water to give 1-(2-carboxychromon-5-yloxy)-2-hydroxy-3-(m-trifluoromethylphenoxy) propane sodium salt (14.25 g) as shiny white flakes, m.p. 235°–237° C.

Analysis: Found: C, 49.90%; H, 3.66%; F, 12.41%. $C_{20}H_{14}F_3O_7Na.2H_2O$ requires: C, 49.80%; H, 3.76%; F, 11.82%.

EXAMPLE 60

1-(2-Acetyl-3-hydroxyphenoxy)-2-Hydroxy-3-(2,4-dichlorophenoxy)propane.

A solution of 2,6-dihydroxyacetophenone (30.4 g), 2,4-dichloro -phenylglycidyl ether (43.8 g), and benzyltrimethylammonium hydroxide (20 drops of 40% solution) in 2-ethoxyethanol (150 ml) was heated under reflux for 60 hours. The solvent was then removed under reduced pressure to give a yellow oil. This was triturated with ether to give a solid which was filtered, washed with ether, dried, and crystallized from ethanol to yield 1-(2-acetyl-3-hydroxyphenoxy)-2-hydroxy-3-(2,4-dichlorophenoxy) propane (36.1 g) as yellow needles, m.p. 130°–132° C.

Analysis: Found: C, 54.85%; H, 4.32%; Cl, 19.04%. $C_{17}H_{16}Cl_2O_5$ requires: C, 55.1%; H, 4.35%; Cl, 19.11%.

EXAMPLE 61

1-(2-Carbethoxychromon-5-yloxy)-2-Hydroxy-3-(2,4-dichlorophenoxy) propane.

A suspension of 1-(2-acetyl-3-hydroxyphenoxy)-2-hydroxy-3-(2,4-dichlorophenoxy) propane (29.6 g) in diethyl oxalate (30 ml) was added to a suspension of sodium ethoxide, prepared from sodium (6.0 g) and ethanol (60 ml) in dry ether (400 ml). The resulting mixture was heated under reflux for 2 hours, cooled, and then poured onto ice (200 g). After acidifying with a solution of acetic acid (24 ml) in water (160 ml) the ethereal layer was separated. The aqueous layer was extracted with ether (3 × 50 ml) and the combined extracts evaporated to give a red oil. This was dissolved in ethanol (96%, 100 ml) containing hydrochloric acid (10 drops) and the solution heated under reflux for 1 hour. The solvent was then removed under reduced pressure to give a red oil which was solidified by triturating with ether. This solid was crystallized from ethanol to yield 1-(2-carbethoxychromon-5-yloxy)-2-hydroxy-3-(2,4-dichlorophenoxy) propane (30.5 g) as cream crystals m.p. 98°–100° C.

Analysis: Found: C, 55.18%; H, 4.23%; Cl, 15.24%. $C_{21}H_{18}Cl_2O_7$ requires: C, 55.6%; H, 4.01%; Cl, 15.64%.

EXAMPLE 62

1-(2-Carboxychromon-5-yloxy)-2-Hydroxy-3-(2,4-dichlorophenoxy) propane Sodium Salt A solution of sodium hydroxide (1.6 g) in ethanol (50 ml) was added with stirring to a hot solution of 1-(2-carbethoxychromon-5-yloxy)-2-hydroxy-3-(2,4-dichlorophenoxy) propane (18.12 g) in ethanol (96%, 100 ml). The resulting suspension was heated under reflux for 1 hour, then cooled and the precipitate filtered off, washed with ethanol, and dried. It was then dissolved in hot water, the solution charcoaled, filtered and allowed to cool. The precipitate was filtered off and dried, yielding 1 (2-carboxychromon-5-yloxy)-2-hydroxy-2-(2,4-dichlorophenoxy) propane sodium salt (11.9 g) as a grey-white solid, m.p. 231°–233°C.

Analysis: Found: C, 47.47%; H, 3.37%; Cl, 14.23%. $C_{19}H_{13}Cl_2O_7Na.2H_2O$ requires: C, 47.22%; H, 3.55%; Cl, 14.67%.

EXAMPLE 63

1-(2-Acetyl-3-hydroxyphenoxy)-2-Hydroxy-3-(p-fluorophenoxy)propane.

A solution of 2,6-dihydroxyacetophenone (30.4 g), p-fluorophenylglycidyl ether (33.6 g), and benzyltrimethylammonium hydroxide (1 ml of a 40% solution) in 2-ethoxyethanol (150 ml) was heated under reflux for 48 hours. After removal of solvent under reduced pressure, the residual viscous oil was triturated with ether, filtered of, and washed with ether to give a yellow powder. Crystallization from aqueous ethanol gave 1-(2-acetyl-3-hydroxyphenoxy)-2-hydroxy-3-(p-fluorophenoxy)propane (39.2 g) as cream needles m.p. 111°–113°C.

Analysis: Found: C, 63.68%; H, 5.48%; F, 5.89%. $C_{17}H_{17}FO_5$ requires: C, 63.74%; H, 5.35%; F, 5.93%.

EXAMPLE 64

1-(2-Carbethoxychromon-5-yloxy)-2-Hydroxy-3-(p-fluorophenoxy)propane.

A suspension of 1-(2-acetyl-3-hydroxyphenoxy)-2-hydroxy-3-(p-fluorophenoxy) propane (25.6 g) in diethyl oxalate (30 ml) was added to a suspension of sodium ethoxide, prepared from sodium (6.0 g) and ethanol (60 ml) in dry ether (400 ml). The mixture was then heated under reflux for 2 hours, cooled, and poured onto ice (200 g). After acidification with a solution of acetic acid (24 ml) in water (160 ml), the ethereal layer was separated, and the aqueous layer was extracted with ether (3 × 50 ml). The organic extracts were combined and concentrated under reduced pressure to give yellow oil. This was dissolved in ethanol (100 ml) containing hydrochloric acid (10 drops) and the solution heated under reflux for 1 hour. After removal of the solvent under reduced pressure the yellow residue was crystallized from ethanol to give 1-(2-carbethoxy-phenoxy)-2-hydroxy-3-(p-fluorophenoxy) propane (22.0 g) as cream crystals, m.p. 112°–114°C.

Analysis: Found: C, 62.61%; H, 4.89%; F, 4.80%. $C_{21}H_{19}FO_7$ requires: C, 62.68%; H, 4.76%; F, 4.72%.

EXAMPLE 65

1-(2-Carboxychromon-5-yloxy)-2-Hydroxy-3-(p-fluorophenoxy)propane Sodium Salt

A solution of sodium hydroxide (1.6 g) in ethanol (96%, 50 ml) was added slowly with stirring to a hot solution of 1-(2-carbethoxychromon-5-yloxy)-2-hydroxy-3-(p-fluorophenoxy) propane (16.08 g) in ethanol (96%, 100 ml). The resulting suspension was heated under reflux for 1 hour, then cooled, and the precipitate filtered off, washed with a little ethanol, and dried. The cream solid was then dissolved in hot water. On cooling, 1-(2-carboxychromon-5-yloxy)-2-hydroxy-3-(p-fluorophenoxy) propane sodium salt (15.0 g) crystallized as a white solid, m.p. 228°–230°C.

Analysis: Found: C, 56.20%; H, 3.76%; F, 4.72%. $C_{19}H_{14}FO_7Na.1/2H_2O$ requires: C, 56.30%; H, 3.73%; F, 4.69%.

EXAMPLE 66

1-(2-Acetyl-3-hydroxyphenoxy)-2-Hydroxy-3-(4-Cyano-3-methoxyphenoxy)propane.

A solution of 2,6-dihydroxyacetophenone (7.6 g), 4-cyano-3-methoxyphenylglycidyl ether (10.25 g) and benzyltrimethylammonium hydroxide (5 drops of a 40% solution) in 2-ethoxyethanol (37.5 ml) was heated under reflux for 48 hrs. After removal of the solvent under reduced pressure, a beige solid remained. This was triturated with ether, filtered, and washed with a mixture of ethanol and ether to yield 1-(2-acetyl-3-hydroxyphenoxy(-2-hydroxy-3-(4-cyano-3-methoxyphenoxy)propane (12.15 g) as a primrose solid, m.p. 155°–157°.

EXAMPLE 67

1-(2-Carbethoxychromon-5-yloxy)-2-Hydroxy-3-(4-Cyano-3-methoxyphenoxy)propane

A suspension of 1-(2-acetyl-3-hydroxyphenoxy)-2-hydroxy-3-(4-cyano-3-methoxyphenoxy) propane (11.9 g) in diethyl oxalate (12.4 ml) was added to a suspension of sodium ethoxide, prepared from sodium (2.3 g) and ethanol (25 ml), in dry ether (200 ml).

Dimethyl sulphoxide (100 ml) was then added to dissolve the solid, and the solution was heated under reflux for 2.5 hours, then cooled and poured onto ice (100 g). After acidification with a solution of acetic acid (12 ml) in water (80 ml), the ether layer was separated and the aqueous layer was extracted with ether (4 × 150 ml). The solvent was then removed from the combined organic layers under reduced pressure, and the residue was dissolved in ethanol (100 ml) to which hydrochloric acid (1 ml) was added. The solution was heated under reflux for 1 hour, then cooled and the solvent removed to give a yellow gum. Trituration with an ether-ethanol mixture gave a yellow solid (10.2 g). This was recrystallized twice from ethanol to give 1-(2-carbethoxychromon-5-yloxy)-2-hydroxy-3-(4-cyano-3-methoxyphenoxy)propane (4.3 g) as an off-white solid, m.p. 143°–145°.

EXAMPLE 68

1-(2-Carboxychromon-5-yloxy)-2-Hydroxy-3-(4-Cyano-3-methoxyphenoxy)propane Sodium Salt A solution of sodium hydroxide (0.4 g) in ethanol (25 ml) was added slowly to a hot suspension of 1-(2-carbethoxychromon-5-yloxy)-2-hydroxy-3-(4-cyano-3-methoxyphenoxy)propane (4.3 g) in ethanol (50 ml). The mixture was then heated under reflux for 1 hour. The resulting suspension was filtered hot, and washed with a little hot ethanol and dried. The residue was dissolved in water, and the solution charcoaled, filtered, and freeze-dried. Washing the product again with hot ethanol gave 1-(2-carboxychromon-5-yloxy)-2-hydroxy-3-(4-cyano-3-methoxypehnoxy)propane sodium salt (3.0 g) as a white solid, m.p. 259°–261°.

EXAMPLE 69

Antiallergic Activity of Representative Compounds

Compounds representative of the above examples were evaluated for antiallergic activity in the rat by the passive cutaneous anaphylaxis test (hereafter PCA), utilizing egg albumin as the antigen.

PCA is an experimentally induced allergic reaction which develops in the skin of test animals after intravenous injection of an antigen. The intensity of such PCA reaction is assessed by measuring the diameters of wheals which develop in the skin of the test animal. Details of the PCA test can be found in the following references: I. Motar, Life Sciences, 1:465 (1963); and B. Ogilvie, Immunology, 12:113 (1967).

In the following table, $ID_{50}$ is the dose which reduced the diameter of the wheel by 50% when injected intravenously together with the antigen. At least 3 groups of 5 rats were used to determine the $ID_{50}$ for each compound tested. The reference compound utilized was disodium chromoglycate (DSCG). The test compounds are identified by their respective Example Numbers above.

| Test Compound by Example Number | $ID_{50}$ ($\mu$ moles/kg) |
| --- | --- |
| 4 | 6.25 |
| 8 | 6.50 |
| 11 | 5.50 |
| 15 | 20.00 |
| 19 | 7.00 |
| 34 | 2.50 |
| 35 | 0.75 |
| 38 | 3.60 |
| 41 | 14.00 |

-continued

| Test Compound by Example Number | $ID_{50}$ ($\mu$ moles/kg) |
| --- | --- |
| 44 | 8.25 |

EXAMPLE 70

Duration of Antiallergic Activity

The duration of antiallergic activity of compounds representative of the above examples was also determined by the PCA test described in Example 66. In each case, 25 $\mu$ moles of the test compound were administered 10 minutes before injection of the egg albumin antigen in rats. The following table reports the mean reactions diameters of wheals in milimeters for the compounds described in the above Examples and disodium cromoglycate (DSCG). In order to achieve maxium significance of results, the effect of each compound was compared directly with DSCG using groups of 10 animals selected at random from the same population.

| Test Compound by Example Number | Mean Reaction Diameters in Milimeters | |
| --- | --- | --- |
| | After 25 $\mu$ moles/kg of Test Compound | After 25 $\mu$ moles/kg of DSCG |
| 4 | 13.0 ± 0.3 | 13.4 ± 0.3 |
| 8 | 6.4 ± 0.4 | 10.6 ± 0.7 |
| 11 | 2.8 ± 0.4 | 10.6 ± 0.7 |
| 15 | 11.0 ± 0.5 | 10.6 ± 0.7 |
| 19 | 10.3 ± 0.2 | 9.7 ± 0.3 |
| 35 | 8.9 ± 0.7 | 8.9 ± 0.8 |
| 38 | 11.2 ± 0.3 | 9.7 ± 0.3 |
| 44 | 6.1 ± 0.4 | 8.6 ± 0.3 |
| 57 | 8.4 ± 0.5 | 8.6 ± 0.3 |
| 62 | 1.3 ± 0.5 | 8.6 ± 0.3 |
| 65 | 12.2 ± 0.2 | 12.3 ± 0.2 |

EXAMPLE 71

Acute Toxicity Tests

Acute toxicity of compounds representative of the above Examples was determined in rats. The test compounds were administered intravenously in either 40 ml/kg of physiological saline or 10 mg/kg of propylene and saline. Compounds which are insoluble in saline were administered in 10 mg/kg of propylene and saline. Animals were observed for one week after administration of the compounds indicated in the following table. Doses administered represent the maximun dose possible and are limited by solubility factors. $ID_{50}$ in the table is used as defined in Example 66. Test compounds are identified by their respective Example Number, above.

| Test Compound by Example Number | DOSE | | Therapeutic Ratio (Dose/$ID_{50}$) |
| --- | --- | --- | --- |
| | mg/kg | $\mu$ mole/kg | |
| 4 | 800 | 2116 | > 339 |
| 8 | 120 | 263 | > 40 |
| 11 | 144 | 341 | > 43 |
| 15 | 532 | 1248 | > 62 |
| 19 | 800 | 2039 | > 281 |
| 34* | 86 | 210 | > 84 |
| 35 | 1000 | 2375 | > 3166 |
| 38 | 286 | 632 | > 173 |
| DSCG | 1000 | 1953 | > 1149 |

*1 propylene glycol/saline

What is claimed is:

1. In a method of prophylactically treating allergic asthma in a mammal in need thereof by inhalational administration of a compound effective in said treatment, the improvement comprising:

prophylactically administering a compound selected from the group consisting of 1-(2-carboxychromon-5-yloxy)-2-(hydroxy)-3-(p-cyanophenoxy)-propane or a nontoxic, pharmacologically acceptable salt thereof to the mammal in an amount effective to treat said asthma.

2. The method as in claim 1 wherein the compound is 1-(2-carboxychromon-5-yloxy)-2-hydroxy-3-phenoxy-propane sodium salt.

* * * * *